United States Patent [19]

Wu et al.

[11] Patent Number: 4,676,984

[45] Date of Patent: Jun. 30, 1987

[54] REHYDRATABLE ANTACID COMPOSITION

[75] Inventors: Chien-Chin Wu, Wilmington, Del.; Gerald L. Reuter, Plattsburgh; Mark E. Coons, Champlain, both of N.Y.

[73] Assignee: American Home Products Corp. (Del), New York, N.Y.

[21] Appl. No.: 765,898

[22] Filed: Aug. 14, 1985

[51] Int. Cl.$^4$ .............................................. A61K 33/08
[52] U.S. Cl. ..................................... 424/157; 424/158
[58] Field of Search ................................. 424/158, 157

[56] References Cited

U.S. PATENT DOCUMENTS

| | | | |
|---|---|---|---|
| 4,112,072 | 9/1978 | Rubino et al. | 424/158 |
| 4,115,553 | 9/1978 | Rubino et al. | 424/158 |
| 4,117,116 | 9/1978 | Buehler et al. | 424/158 |

OTHER PUBLICATIONS

Handbook of Nonprescription Drugs, Fifth edition, p. 16, Amer. Phar. Assoc., Wash. D.C.

*Primary Examiner*—Frederick E. Waddell

[57] ABSTRACT

An rehydratable antacid composition of magaldrate gel and a process for preparing same are described by the invention. The composition is prepared from and contains precipitated and undried magaldrate gel, a polyhydric alcohol and fluidizing amounts of a first and second fluidizer. One fluidizer is provided by an aluminum hydroxide gel having colloidal properties and the second by a pharmaceutically acceptable citrate ion source including citric acid. The process and composition are characterized in providing rehydratable antacid composition which when admixed with water forms a fluid, resuspendible, pharmaceutically elegant suspension possessing high antacid capacity and stability at even elevated magaldrate concentrations in addition to the ability to fluidize stiff, paste-like magaldrate gel cakes.

7 Claims, No Drawings

REHYDRATABLE ANTACID COMPOSITION

BACKGROUND OF THE INVENTION

1. Field of the Invention

This invention relates to magaldrate antacid powder compositions which are rehydratable to form pharmaceutically elegant high and low concentration, pourable, aqueous antacid suspension dosage forms for oral administration and to methods for their preparation and use.

2. Description of the Antacid Art

Antacids are widely used in the treatment of gastrointestinal disorders. Their effectiveness in promoting the healing of gastric and duodenal ulcers has been well documented. Essentially, antacids exert their positive effects by neutralizing the gastric acid secreted in the stomach. When the pH of stomach contents is raised above 3, most gastric acid is neutralized and the proteolytic activity of pepsin is inhibited. The recent elevation of antacids to a major therapeutic role, particularly in ulcer therapy, rather than a merely palliative role, has emphasized the importance of providing antacid products featuring a high neutralization (and buffer) capacity as well as a rapid rate of gastric acid neutralization. These features, particularly that of rapid rate of neutralization to the neutralization capacity of the antacid, define the more effective antacid in vivo since it is less likely that non-reacted antacids will be removed by normal gastric emptying.

Most antacids are available in both liquid and solid dosage forms. The liquid antacids, as aqueous suspensions, are, generally, more effective than the same antacids in solid dosage forms and are more commonly prescribed in the hospital. The greater effectiveness of liquid antacids is partially due to the large surface area available in liquid suspensions to react with gastric acid and partially due to the great amount of colloidal particles in aqueous suspensions which can more easily reach the affected area where treatment is needed. Moreover, aqueous suspensions of not previously dried antacids are more reactive than dry or solid antacids.

While liquid antacids possess these advantages, the same require administration of relatively large volumes of liquid suspension. The ingestion of such large volumes is inconvenient, however, making the normal problem of assuring patient compliance outside the hospital environment even more difficult. Since high dose regimens of liquid antacid have recently been shown to be effective both in promoting the healing of duodenal ulcers and in preventing the acute upper gastrointestinal bleeding in critically ill patients, the use of regular liquid antacid suspensions with the usual antacid content in the 6-12 percent range has become even more impractical for such therapeutic indications.

The most widely used antacids can be described as mineral type, insoluble inorganic salts that are hydrated, possess colloidal properties, and contain, for example, aluminum, magnesium, bismuth and the like. Compounds of the described mineral variety in their freshly prepared, hydrated form and in suspensions therefrom provide some of the characteristics desired in an antacid. To provide liquid antacids with a high neutralization capacity it is necessary to increase the solids concentration of the antacid components. Such increases in concentration, however, are accompanied at higher levels with exponential increases in viscosity, a loss in colloidal properties and a loss of fluidity or mobility. Even when fluidity is initially maintained or achieved, further requirements of pharmaceutically acceptable aqueous antacid suspensions call for a smooth (non-gritty) mouth feel and maintenance of a gel structure for both suspendibility and resuspendibility. In general, resuspendible, aqueous antacid suspensions are typically partially de-flocculated products which contain a deflocculant and suspending agent to arrest or control further agglomeration or flocculation and settling. In the absence of a deflocculant and suspending agent type additive, the antacid in a suspension forms a hard cake or a gel structure which can no longer be resuspended with its original desirable characteristics.

Thus deflocculants and suspending agents have been frequently included in the formulation of aqueous antacid suspensions containing solid antacid concentrations in the range of about 6 to 12 percent to prevent caking. With the growing interest in providing antacid suspension dosage forms with a greater acid neutralizing capacity, means were sought to provide highly concentrated but fluid systems.

Although it has been reported that liquid antacids take effect faster and provide longer duration than the same antacids in solid dosage form, some disadvantages also exist in the preparation of liquid antacids. For example, high pH value (8-10) of the antacid suspension makes the microbial preservation of this product a difficult task. Most preservatives which are suitable for ingestion are not stable or effective in this pH range. In aging, some antacid gels could change from an active amorphous form to a less active crystalline form. As liquid antacids contain about 80-90% of water, they are not only inconvenient to use but also sensitive to both microbial contamination and temperature change. The cost of package, shipment and storage is more expensive for liquid than solid antacids. Therefore, it would be useful to develop an antacid powder which can be reversibly converted to its original colloidal state when wetted with water.

When magaldrate is precipitated by adding the magnesium salt to the alkali aluminate solution, it is a white gel containing 6-15% solids. The spray dried powder of this gel is not rehydratable to a smooth suspension. When wetted with water, the powder remains intact and can not go back to its colloidal state. This powder appears less effective and tastes gritty. Therefore, there is a need in the art for a totally rehydratable magaldrate powder which can be easily formulated, shipped to a distant facility, stored for a period of time and reconstituted to a colloidal suspension when it is needed.

Copending application Ser. No. 661,648, filed Oct. 17, 1984 in the names of Wu and Reuter and entitled "Fluidized Magaldrate Suspension", herein incorporated by reference in its entirety, describes and claims an aqueous antacid composition characterized in providing a fluid, resuspendible, pharmaceutically elegant antacid suspension with high antacid capacity comprising precipitated and undried magaldrate gel and a fluidizing amount of a combination of an aluminum hydroxide gel having colloidal properties as a first fluidizer and a second fluidizer selected from at least one of the group consisting of citric acid and a pharmaceutically acceptable citrate ion source.

It has now been found that the composition disclosed and claimed in copending application Ser. No. 661,648 after addition of a polyhydric alcohol can be dehydrated to form a dry rehydratable magaldrate composition.

It is therefore an object of this invention to provide rehydratable magaldrate compositions in solid powder form which when admixed with water form aqueous antacid suspensions with high antacid capacity and good mouth feel characteristics.

Another object of this invention is to provide rehydratable magaldrate compositions in solid powder form which when admixed with water form aqueous antacid suspensions with high antacid capacity and which retain, at high concentrations, the desirable qualities of rapid acid neutralization and reliably uniform reaction in acidic solutions.

A further object of the invention is to provide high antacid capacity, rehydratable magaldrate compositions in solid powder form, which when admixed with water form suspensions with good fluidity, pourability and suspension characteristics and which further provides full resuspendibility under the typical shelf life conditions for a commercial aqueous antacid suspension, and which can also be formulated into chewable tablets with reduced grittiness when ingested.

SUMMARY OF THE INVENTION

In accordance with this invention there is provided rehydratable magaldrate compositions in solid powder form which when admixed with water form aqueous antacid compositions characterized in providing a fluid, resuspendable, pharmaceutically elegant antacid suspension with high antacid capacity. The composition comprises precipitated and codried magaldrate gel, a fluidizing amount of a combination of an aluminum hydroxide gel having colloidal properties as a first fluidizer and a second fluidizer selected from at least one of the group consisting of citric acid and a pharmaceutically acceptable citrate ion source, and a polyhydric alcohol.

In another embodiment, the invention includes a method for producing rehydratable antacid compositions of high antacid capacity and which are characterized in providing fluid, resuspendible pharmaceutically elegant antacid suspensions of magaldrate. The method comprises mixing a precipitated and undried magaldrate gel with a fluidizing combination of a first and second fluidizer and a polyhydric alcohol. The first fluidizer is selected from an aluminum hydroxide gel having colloidal properties and the second fluidizer is selected from at least one of the group consisting of citric acid and a pharmaceutically acceptable citrate ion source. The method for producing the high antacid capacity, aqueous antacid compositions of the invention may be broadly approached and achieved, for example, either by prior concentration of the magaldrate gel cake into a high concentration paste followed by its fluidization with a fluidizing amount of the combination of the first and second fluidizer, or, by concentration of a fluid and relatively low concentration magaldrate gel cake previously mixed with a fluidizing amount of the combination of the first and second fluidizer. The resulting admixture is then dehydrated or dried to form the desired rehydratable antacid composition.

The magaldrate of the invention is the precipitated, undried form of the antacid. This description refers to magaldrate gel which has not been previously dried to its hydrated, anhydrous form.

DETAILED DESCRIPTION OF THE INVENTION

Magaldrate is a chemical combination of aluminum and magnesium hydroxide, corresponding approximately to the formula $Al_5Mg_{10}(OH)_{31}(SO_4)_2xH_2O$, according to the official monograph USP XX, third supplement USP-NF, and has a molecular weight of about 1097.4. Magaldrate, also sometimes referred in said monograph as aluminum magnesium hydroxidesulfate, contains not less than 29.0 percent and not more than 40.0 percent of magnesium oxide (MgO) and the equivalent of not less than 18.0 percent and not more than 26.0 percent of aluminum oxide ($Al_2O_3$).

The preparation of magaldrate is described in U.S. Pat. No. 2,923,660. A commercially suitable procedure is described in said patent, for example, beginning in column 2, line 40. Aluminum sulfate is employed as at column 2, line 58 in order to obtain a magaldrate "all sulfate" material and, to maintain a low sodium content for the final product, the use of potassium oxide (or hydroxide) is preferred over the disclosed sodium oxide. Typically the magaldrate is precipitated to provide a 6% weight/volume mixture (fluid when fresh) and diluted to 3% for washing prior to concentration and formulation into a suspension providing a so called single strength neutralization capacity (ANC) of 13.5 to 15 meq per 5 milliliters of suspension which is equivalent to a magaldrate weight/weight concentration in the range of about 12 to 13 percent solids. At this concentration, unformulated, magaldrate is a paste-like gel.

Mere fluidization or defloculation of an aqueous suspension dosage is, however, only one factor in the formulation of an aqueous antacid suspension. Thus, no advantage arises from increased fluidization or more highly concentrated suspension if fluidization is achieved at the expense of resuspendibility or loss of rate or extent of acid neutralization capacity or antacid buffer capacity, immediately or upon aging. This concern is especially acute for an aqueous antacid suspension comprising magaldrate as the predominant antacid because of its exceptional balance of desirable antacid properties within a single chemical entity—i.e., rapid reaction rate, prolonged buffering action within the therapeutically desired range and good acid-consuming capacity. With this invention, the desirable balance of magaldrate antacid properties is retained while the rheological properties of the magaldrate gels are significantly altered, thereby enabling the provision of concentrated, high antacid capacity magaldrate suspension. An additional benefit accompanying this invention is the uniformity of desirable rheological properties obtained which reduces or eliminates the batch to batch fine tuning frequently required to deal with the unpredictability usually inherent in the rheological properties of both fluidized and unfluidized magaldrate gels.

As previously described the magaldrate gel of this invention refers to precipitated magaldrate which has not previously been dried to its hydrated, anhydrous form. While the fluidizing combination contained in the composition of the invention may very well fluidize an aqueous mixture employing anhydrous magaldrate gel, a composition therefrom will not possess the desirable combination of suspension, resuspendability, colloidal and antacid properties provided by the composition of the invention. Moreover, it is preferred in the composition of the invention to utilize freshly precipitated magaldrate gel since the use of older gels appears to require relatively higher proportions of the fluidizing combinations than the same composition comprising freshly precipitated magaldrate gels.

In contrast to most currently available antacid suspensions and to commercial magaldrate antacid suspensions which provide an ANC of about 13.5 meq/5 ml, the rehydratable magaldrate compositions of this invention readily provides when admixed with water an antacid composition with an acid neutralization capacity (double strength) of at least 25-30 meq/5 ml or of at least about 17-18% to about 20% weight/weight or about 18 to about 22% weight/volume. It will be appreciated that less concentrated suspensions such as those having an ANC of 13.5 meq/5 ml are, also, easily achievable by the composition and method of this invention. The upper limit to the ANC and concentration of the composition of this invention is only limited by the equipment available, but is believed to be on the order of 50-60 meq/5 ml.

The ratio on a dry basis of magaldrate to the fluidizing combination will range from about 25:1 to about 2:1, and preferrably from about 8:1 to about 4:1. For example, in a composition having 216 g magaldrate per liter of suspension, the 25:1 to 2:1 ratio would correspond to about 8.0 g/l to about 104 g/liter of fluidizers.

The ratio on a dry basis of the first fluidizer, aluminum hydroxide gel, calculated as aluminum oxide to the second fluidizer will range from about 1:15 to about 1:1, preferrably from about 1:6 to about 1:2 and most preferrably in a range of about 1:4. For example, in a composition having 216 g magaldrate per liter of suspension in a ratio to fluidizers of 8:1 or 27 g/l of fluidizers the 1:4 ratio of first fluidizer to second fluidizer would correspond to about 5.4 g/l of first fluidizer and 21.6 g/l of second fluidizer.

The polyhydric alcohols suitable for use in the rehydratable magaldrate compositions of this invention include those having from 2 to 6 free hydroxyl groups and include propylene glycol, glycerol, eriythritol, threitol, ribitol, xylitol arabinitol, glycitol, sorbitol, mannitol and dulcitol. The polyhydric alcohol can be present in amounts of about 5 to about 10% by weight of the composition. Sorbitol is the preferred polyhydric alcohol.

In another embodiment, the invention relates to a method for providing or preparing aqueous antacid compositions of high antacid capacity and which are further characterized in providing rehydratable magaldrate compositions which when admixed with water form fluid, resuspendible pharmaceutically elegant antacid suspensions of magaldrate. The method broadly comprises mixing a precipitated and undried magaldrate gel with a fluidizing combination of the first and second fluidizer of this invention. Moreover, mixing can be done prior or subsequent to concentration of the magaldrate gel.

Thus in one aspect the method of this invention comprises:

(a) mixing a low concentration of a precipitated and undried magaldrate gel with an admixture of a polyhydric alcohol and a fluidizing amount of a combination of an aluminum hydroxide gel having colloidal properties as a first fluidizer and a second fluidizer selected from at least one of the group consisting of citric acid and a pharmaceutically acceptable citrate ion source;

(b) concentrating the mixture of step (a) to a fluid high antacid capacity aqueous magaldrate suspension.

(c) drying the mixture of step (b) as in a spray dryer.

Alternatively, the first two steps of the method of the invention may be reserved so that the magaldrate gel is first concentrated to a concentration providing a high antacid capacity and then fluidized by mixing the concentrate magaldrate gel with a fluidizing amount of a combination of the first and second fluidizer of the invention.

In a preferred embodiment the method of the invention comprises:

(a) forming an aqueous mixture containing a polyhydric alcohol and a fluidizing amount of a combination of an aluminum hydroxide gel having colloidal properties as a first fluidizer and a second fluidizer selected from at least one from the group consisting of citric acid and a pharmaceutically acceptable citrate ion source;

(b) concentrating a precipitated and undried magaldrate gel to high antacid capacity;

(c) incrementally and continuously charging and mixing the concentrated magaldrate gel into a stream of the mixture containing said fluidizers thereby fluidizing the concentrated gel into a fluid suspension; and (d) drying the mixture of step (c) as in a spray dryer.

The concentrations and proportions of materials used in the method of the invention are the same as those described for the composition of the invention and will be based on the magaldrate concentration of the fluidized suspension. Thus, the concentration of the magaldrate in step (b) of the hereinabove described method will exceed the final concentration of the suspensions. Also, as with the composition of the invention, the method of the invention preferably employs freshly precipitated magaldrate gel.

When the rehydratable magaldrate compositions of this invention are rehydrated with water to form antacid suspensions, such compositions include a number of pharmaceutically acceptable excipients which are conventional in the aqueous antacid suspension art and do not form part of the invention. Such excipients include one or more flavoring agents e.g. peppemint, etc; sweetening agents, e.g. saccharin, sorbitol; preservatives; sanitizers; body-building agents and the like.

Antacid suspensions formed from water and the composition of this invention may also contain other therapeutically active substances such as antiflatulents, as for example, simethicone; algin derivatives for treatment of esophogeal reflux; analgesics such as acetaminophen, ibuprofen and protected aspirin; various antidiarrheal or parasympatholytic agents; antiulcer agents such as cimetidine, ranitidine and sucralfate; and others.

Antacid suspensions formed from water and compositions of this invention are useful in the treatment of a variety of gastrointestinal disorders in man or animals. Typical of such disorders are hyperchlorhydria, peptic ulcer, gastric ulcer, duodenal ulcer, gastritis, esophagitis, hiatal hernia, and other digestive disturbances. As noted earlier, the antacid suspensions formed from the compositions of this invention are especially useful in the treatment of disorders that demand the antacid to play a therapeutic role rather than a mere palliative role. The dosage form of the antacid suspension formed from the composition of this invention will normally be administered orally. In general, the therapeutic dosage of the composition can be determined by relationship to the ANC of same to that of known antacid dosage forms.

While not wishing to be bound by any theory of invention, it is hypothesized that magaldrate prepared by the processes earlier described, contains small particles with a resulting greater surface area and higher surface charges. With a material such as just described, one in which it is essential to maintain the colloidal properties of the magaldrate to guarantee its most efficacious values over a useful shelf-life, control of viscosity is critical, and, is rendered more difficult in increasing concentrations. This control is achieved with a fluidizing amount of a combination of the first and second fluidizer whereby the second fluidizer apparently controls the surface charge of the magaldrate to create a desirable negative influence while the first fluidizer apparently enhances the arion adsorption process and provides a competitive substrate with the magaldrate thereby maintaining an equilibrium of the negative influence. The negative influence, which can be determined by zeta potential measurements, thus fluidizes the magaldrate suspension to a mobilizable gel having an equilibrium which apparently provides for retention of desirable properties.

In the following examples a Buchi 190 Mini Spray Dryer was employed to dry the initial admixture containing magaldrate, the polyhydric alcohol and the first and second fluidizers. This model spray dryer is manufactured by Buchi Laboratoriums-Technik AG. Other spray dryers can be employed, however, such as those manufactured by Anhydro Company of Attleboro, Mass. and Niro Atomizer Inc., of Columbia, Md., so long as the spray dryer can process the relatively viscous admixture. The operating conditions for the spray dryer are customarily an inlet temperature of 400° C., an outlet temperature of 130° C. and a wheel speed of 20,000 RPM.

EXAMPLE 1

In this example, a rehydratable magaldrate powder of this invention was prepared having the following formulation:

| INGREDIENTS | AMOUNT |
| --- | --- |
| Magaldrate Gel Sulfate, Potassium Based (7.38%) | 90.0 kg |
| Potassium Citrate, NF | 1.47 kg |
| Aluminum Hydroxide Gel, Guilini, A671/4 | 1.85 kg |
| Sorbitol Solution, USP 70% | 2.85 kg |

The above listed ingredients were processed as set forth below. Continuous agitation must be maintained throughout the processing.

Step 1. Add the sorbitol solution, USP to a suitable tank equipped with a stirrer.

Step 2. Add the potassium citrate, NF then mix until uniform.

Step 3. Concentrate the magaldrate gel sulfate, potassium base to not less than 24% magaldrate and add to the tank in Step #2

Step 4. When approximately half of the concentrated gel has been added to the batch, add the aluminum hydroxide gel to the mixture of Step #3.

Step 5. When all of the gel has been added, obtain an assay of the magaldrate content and adjust the quantities of all ingredients to the theoretical ratios. Mix for 5 minutes after each addition.

Step 6. Spray dry the Step #5 gel mixture at the following conditions:

| Inlet | 400° C. |
| --- | --- |
| Outlet | 130° C. |
| Wheel Speed | 20,000 RPM |

EXAMPLE 2

In this example, the rehydratable magaldrate powder of Example 1 was reconstituted into a stable, liquid magaldrate formulation for oral administration containing 15 milliequivalents of magaldrate per 5 milliliters of formulation. In this and the following examples the monochloroamine solution employed was a stock solution prepared in the following manner from the listed ingredients.

| Monochloramine Solution | |
| --- | --- |
| INGREDIENTS | AMOUNT |
| Calcium Hypochlorite, 60% | 14.00 g |
| Ammonia Solution, Strong, NF | 7.4 g |
| Water, Purified, USP, Chlorinated | 28.0 g |
| Water, Purified, USP, Chlorinated | 1.97 kg |

The calcium hypochlorite, 60% was added to 1.97 kg water and mixed with vigorous stirring for at least 10 minutes. The ammonia solution was added to 28.0 g water and stirred briefly. The ammonia solution was then added to the chlorine solution and mixed with vigorous stirring until uniform and filtered after an hour.

Using the rehydratable magaldrate powder as prepared in Example 1, the monochloroamine solution prepared as shown above, and the other ingredients shown below, the reconstituted magaldrate was prepared as follows:

| INGREDIENTS | AMOUNT |
| --- | --- |
| Rehydratable Magaldrate, Spray Dried 64% w/w | 168.75 g* |
| Glycerin, USP | 23.9 g |
| Saccharin, NF | 0.383 g |
| Peppermint Flavor #5917 | 0.283 ml |
| Xanthan Gum, FCC | 2.0 g |
| Monochloramine Soln. QS | QS 100 PPM |
| Water Purified, USP Chlorinated | QS 1000 ml = 1100 g |

*Theoretical input per liter is 108 g Magaldrate 100%

The above listed ingredients were processed as set forth below. During processing the equipment should be kept clean to minimize bacterial growth and the processing carried out as aseptically as practicable. The finished suspension should be kept in a closed tank to minimize monochloroamine losses during filling. Also continuous stirring must be maintained throughout.

Step 1. Place 700 grams of chlorinated water into a suitable compounding tank equipped with a mixer.

Step 2. Slowly add the magaldrate powder with constant mixing, mix for approximately 1 hour or until completely hydrated.

Step 3. To a separate container equipped with an agitator, add the Glycerin, saccharin, xanthan gum, and the peppermint flavor and mix until uniform, then cool to 30° C. or less.

Step 4. Add the Step #3 mixture to the Step #2 mixture and mix until the xanthan gum is hydrated.

Step 5. Add sufficient water to bring the batch to 1.0774 kg.

Step 6. Pass the suspension through a homogenizer at 1000 PSIG+100 into a jacketed tank with continuous stirring.

Step 7. Immediately prior to the start of filling, add monochloramine at 6,000 PPM to achieve 100 PPM (NLT 85) by assay in the bulk suspension and mix for 30 minutes. The suspension of step 7 should be below 25° C. before adding the monochloramine.

Step 8. Fill the finished suspension into bottles with screw cap which may have been previously sterilized.

Step 9. Invert each bottle of suspension for not less than 2 seconds (NMT 1 hour), then return to the upright position.

EXAMPLE 3

In this example, the rehydratable magaldrate powder of Example 1 was reconstituted into a stable, liquid magaldrate formulation for oral administration containing 30 milliequivalents of magaldrate per 5 milliliters of formulation.

Using the rehydratable magaldrate powder as prepared in Example 1, the monochloroamine solution prepared as shown in Example 2, and the other ingredients shown below, the reconstituted magaldrate was prepared as follows:

| INGREDIENTS | AMOUNT |
|---|---|
| Rehydratable Magaldrate, Spray Dried 64% w/w | 337.55 g* |
| Glycerin, USP | 47.8 g |
| Simethicone, USP 95% w/w | 6.32 g |
| Saccharin, NF | 0.383 g |
| Peppermint Flavor #5917 | 0.283 ml |
| Xanthan Gum, FCC | 3.5 g |
| Monochloramine Soln. QS | QS 1000 ml = 1200 g |

*Theoretical input per liter is 216 g Magaldrate 100%

The above listed ingredients were processed in the same manner as in Example 2 except that in Step 1 only 500 grams of chlorinated water was placed in the mixer, the simethicone was added and mixed after Step 4, and in Step 5, sufficient water was added to bring the batch to only 1.0774 kg.

EXAMPLE 4

In this example, a rehydratable magaldrate composition of this invention was prepared having the following formulation to produce 100 kg of magaldrate powder.

| INGREDIENTS | AMOUNT |
|---|---|
| Magaldrate Gel Sulfate, Potassium Based (7.38%) | 908 kg |
| Potassium Citrate, NF, Granular | 9.4 kg |
| Aluminum Hydroxide Gel, Giulini A671/4 12% | 11.8 kg |
| Sorbitol Solution, USP 70% | 29.4 kg |
| Water, Purified, USP, Chlorinated | 5.7 kg |

Typical condition for spray drying:
 Inlet Temperature-400° C.
 Outlet Temperature-130° C.
 Atomization Wheel Speed 16,000 RPM Magaldrate concentration of resultant powder would typically range from 65-68%.

EXAMPLE 5

A magaldrate chew tablet prepared from the rehydratable powder of Example 4 sufficient to make 1000 directly compressed tablets is shown below:

| INGREDIENTS | AMOUNT |
|---|---|
| Magaldrate Rehydratable Spray Dried Powder 67% | 806.0 g |
| Mannitol, USP | 290.5 g |
| Nu-tab (a directly compressible sugar) | 290.5 g |
| Flavor-Spearmint, Aromalok | 6.0 g |
| Magnesium Stearate | 7.0 g |
| Theoretical Tablet Weight | 1,400 mg |

Other examples of directly compressible tabletting ingredients for this product would be dextrates, sorbitol and other directly compressible sugars such a Di-Pac, a compressible sucrose made by Amstar Corporation of New York, N.Y. Zinc Stearate could also be substituted as a lubricant for magnesium stearate. A lozenge dosage form rather than a chew tablet can be prepared using suitable tabletting ingredients such as sorbitol.

EXAMPLE 6

Magaldrate rehydratable granules can be prepared from the rehydratable powder of Example 4 to provide 1 kilogram of granulation as follows:

| INGREDIENTS | AMOUNT |
|---|---|
| Magaldrate Rehydratable Spray Dried Powder 67% | 700.0 g |
| Sugar Confectioners, NF | 300.0 g |
| Water, Purified, USP, Chlorinated | 150.0 ml |

The above powders are wet massed in a suitable mixer by the addition of water. The resultant granulation is wet sized, dried in a fluidized bed dryer and then dry sized. The potency of the above resultant granulation is 46.9% magaldrate.

EXAMPLE 7

The rehydratable magaldrate granules as prepared in Example 6 can be packaged to provide a 30 milliequivalent magaldrate dose per 5 milliliters of oral dosage form as follows:

| INGREDIENTS | AMOUNT |
|---|---|
| Magaldrate Rehydratable Granules 46.9% | 2.3 g |
| Flavor, Spearmint, Aromalok | 0.004 g |

To the above blend, one would add 5 ml water and shake to rehydrate. This would give a single 30 mEq dose.

EXAMPLE 8

The rehydratable magaldrate granules as prepared in Example 6 can also be packaged with milk solids to provide a 30 milliequivalent magaldrate dose per 20 milliliters of oral dosage form as follows:

| INGREDIENTS | AMOUNT |
|---|---|
| Magaldrate Rehydratable Granules 46.9% | 2.3 g |
| Milk Solids (Instant Non-Fat Dry Milk) | 0.7 g |
| Flavor-Spearmint, Aromalok | 0.006 g |

Again for a single dose, 20 ml of water would be added to the above blend to allow for rehydration. The milk solids are added to give a creamier and more pleasant tasting product.

EXAMPLE 9

The rehydratable magaldrate granules as prepared in Example 6 can further be packaged with other pharmaceutical agents such as antidiarrhea agents, i.e. adsorbents and anticholinergics, as follows:

| INGREDIENTS | AMOUNT |
|---|---|
| Magaldrate Rehydratable Granules 46.9% | 1,150 mg |
| Kaolin (hydrated aluminum silicate) | 1,000 mg |
| Hyoscine Hydrobromide | 0.002 mg |

The mixture would be rehydrated and resuspended with 20 ml water for a single dose (ANC of 15 mEq).

The packaging of the compositions of Examples 7–9 preferably would be of the foil or hermetic unit type.

Additional formulation of rehydratable magaldrate powder are shown in Table 1.

TABLE 1

In each of the formulae, one kilogram of 13.6% magaldrate gel fresh off the artisan was employed. The other ingredients are as shown in grams.

| Formula | 1 | 2 | 3 | 4 | 5 | 6 | 7 | 8 | 9 | 10 | 11 | 12 |
|---|---|---|---|---|---|---|---|---|---|---|---|---|
| Potassium Citrate | 19.12 | 15 | 10 | 25 | 30 | 5 | 19.72 | 30 | 19.72 | 19.12 | 10 | 30 |
| Al(OH)$_3$ Fluid Gel | 24.89 | 18.9 | 12.62 | 31.55 | 37.86 | 37.86 | 24.89 | 37.86 | 24.89 | 24.89 | 12.63 | 37.86 |
| Sorbitol 100% | 59.29 | 59.29 | 59.29 | 59.29 | 59.29 | 59.29 | 77.71 | 77.71 | 97.14 | 59.29 | 59.29 | 59.29 |
| Saccharin NF | — | — | — | — | — | — | — | — | — | .383 | .383 | .383 |

PROCEDURE
1. To the small Hobart mixing bowl add the magaldrate gel, potasium citrate, Al(OH)$_3$, sorbitol, and saccharin NF, if in formula and mix until uniform.
2. Add 100 PPM monochloramine to Step #1 and mix.
3. Dry on Buchi 190 Mini Spray Dryer.

Of the rehydratable magaldrate powder compositions of Table 1, Formula 8 gave the best mouth feel in terms of no grittiness and Formula 6 was next best. All of the formulas were readily rehydratable.

We claim:

1. An antacid composition in solid powder form characterized by providing when admixed with water a fluid, resuspendable, pharmaceutically elegant antacid suspension with high antacid capacity of at least about 25 milliequivalents of said neutralizing capacity per 5 milliliters of suspension comprising:

the co-dried admixture of
(a) at least about 18% by weight based upon the weight of the admixture prior to being dried of magaldrate gel in its freshly precipitated wet state containing at least about 24% by weight of magaldrate;
(b) about 5% to about 10% by weight of a polyhydric alcohol based on the weight of the admixture prior to being dried, and
(c) a fluidizing amount of a combination of (i) as a first fluidizer an aluminum hydroxide gel having colloidal properties and (ii) as a second fluidizer potassium citrate, the weight ratio on a dry basis of magaldrate to the combination of fluidizers being within the range of about 25:1 to 2:1 and the weight ratio on a dry basis of the first fluidizer calculated as aluminum oxide and the second fluidizer being within the range of about 1:6 to about 1:2.

2. The composition of claim 1 wherein the polyhydric alcohol contains 2 to 6 free hydroxyl groups.

3. The composition of claim 1 wherein the polyhydric alcohol is sorbitol.

4. The composition of claim 1 wherein the ratio on a dry basis of magaldrate to the combination of fluidizers ranges from about 8:1 to about 4:1.

5. The composition of claim 1 wherein the ratio on a dry basis of the first fluidizer to the second fluidizer is about 1:4.

6. A method for preparing a rehydratable antacid composition of magaldrate gel in solid powder form from a fluidized admixture which before being dried is composed of
(a) at least about 18% by weight based upon the weight of the admixture prior to being dried of magaldrate gel in its freshly precipitated wet state containing at least about 24% by weight of magaldrate,
(b) about 5% to about 10% by weight of a polyhydric alcohol based on the weight of the admixture prior to being dried, and
(c) a fluidizing amount of a combination of (i) as a first fluidizer an aluminum hydroxide gel having colloidal properties and (ii) as a second fluidizer potassium citrate, the weight ratio on a dry basis of magaldrate to the combination of fluidizers being within the range of about 25:1 to 2:1 and the weight ratio on a dry basis of the first fluidizer calculated as aluminum oxide and the second fluidizer being within the range of about 1:6 to about 1:2, comprising the steps of:
(1) forming a mixture containing the polyhydric alcohol, first fluidizer, second fluidizer and citrate ion source;
(2) concentrating the precipitated and undried magaldrate gel to a weight concentration of at least 24%;
(3) incrementally and continuously charging and mixing the concentrated magaldrate gel with a stream of the mixture containing said first fluidizer, second fluidizer and polyol thereby fluidizing the concentrated gel into a fluid suspension; and
(4) drying the fluid suspension of magaldrate gel, polyhydric alcohol and first and second fluidizers.

7. The method of claim 6 wherein the polyhydric alcohol is sorbitol.

* * * * *